(12) United States Patent
Shimizu et al.

(10) Patent No.: US 8,239,991 B2
(45) Date of Patent: Aug. 14, 2012

(54) ELECTRIC-ELECTRONIC TOOTHBRUSH

(75) Inventors: Hiroaki Shimizu, Hikone (JP);
Tomohiro Kunita, Hikone (JP);
Shinichi Taniguchi, Otsu (JP); Suehisa Kishimoto, Hikone (JP); Tadanobu Kitagawa, Hikone (JP)

(73) Assignee: Panasonic Corporation, Kadoma-shi (JP)

( * ) Notice: Subject to any disclaimer, the term of this patent is extended or adjusted under 35 U.S.C. 154(b) by 508 days.

(21) Appl. No.: 12/448,608

(22) PCT Filed: Dec. 25, 2007

(86) PCT No.: PCT/JP2007/074872
§ 371 (c)(1),
(2), (4) Date: Jun. 26, 2009

(87) PCT Pub. No.: WO2008/081790
PCT Pub. Date: Jul. 10, 2008

(65) Prior Publication Data
US 2010/0115718 A1    May 13, 2010

(30) Foreign Application Priority Data
Dec. 27, 2006    (JP) .................................. 2006-352638

(51) Int. Cl.
*A61C 17/22* (2006.01)

(52) U.S. Cl. ............... 15/22.1; 15/22.2; 604/20; 607/79

(58) Field of Classification Search ............... 15/22.1, 15/22.2; 601/21; 604/20; 607/79
See application file for complete search history.

(56) References Cited

U.S. PATENT DOCUMENTS

| | | | |
|---|---|---|---|
| 4,944,296 A | 7/1990 | Suyama | |
| 5,406,664 A | 4/1995 | Hukuba | |
| 2008/0083074 A1* | 4/2008 | Taniguchi et al. | ............. 15/22.1 |

FOREIGN PATENT DOCUMENTS

GB    2317555 A    4/1998
(Continued)

OTHER PUBLICATIONS

Supplementary European Search Report for European Patent Application No. 07860101.0 issued May 17, 2011.

(Continued)

*Primary Examiner* — Mark Spisich
(74) *Attorney, Agent, or Firm* — Edwards Wildman Palmer LLP

(57) ABSTRACT

An electric-electronic toothbrush carries a brush driven to vibrate, and arranged to flow an electric current into a user's oral cavity for promoting removal of tooth plaque. The electric-electronic toothbrush has a shaft driven to vibrate along and/or about an axis of the shaft, and a battery supplying the electric current. The shaft is electrically conductive to flow the electric current into a brush electrode of a brush head. The shaft is electrically connected to the battery by way of an extendible electrically conductive coupler within the handle. The electrically conductive coupler has its one end secured to the shaft, and the other end to an electrically conductive member connected to one of poles of the battery, so as to absorb the vibration of the shaft. The handle is provided on its outer peripheral surface with a touch electrode. The electric-electronic toothbrush is arranged to give predetermined electric potentials respectively to the brush electrode and the touch electrode, so as to flow a microelectric current onto the tooth surface for removal of tooth plaque during user's tooth brushing due to vibration of a brush.

8 Claims, 5 Drawing Sheets

| | FOREIGN PATENT DOCUMENTS | |
|---|---|---|
| JP | 03-261407 | 11/1991 |
| JP | 04-030806 A | 2/1992 |
| JP | 5-184424 | 7/1993 |
| JP | 6-90824 * | 4/1994 |
| JP | 06-237821 A | 8/1994 |
| JP | 2560025 | 9/1996 |
| JP | 10-243820 A | 9/1998 |
| WO | WO-9009206 | 8/1990 |

OTHER PUBLICATIONS

International Search Report and Written Opinion dated Apr. 8, 2008 issued in PCT/JP2007/074872.

* cited by examiner

ELECTRIC-ELECTRONIC TOOTHBRUSH

TECHNICAL FIELD

This invention relates to an electric-electronic toothbrush with a brush driven to vibrate.

BACKGROUND ART

Japanese Patent Publication NO. 2560025 discloses a conventional electric toothbrush. This electric toothbrush has a handle to be grasped by user, a vibration unit accommodated within the handle for vibrating a shaft along its axis. The shaft is detachably connected to a brush head, and driven to vibrate the brush head by the vibration unit. This electric toothbrush is designed to flow a micro-electric current through user's body into portion of a user's oral cavity in contact with the brush head, for removal of tooth plaque. This electric toothbrush is equipped with a source of micro-electric current having one pole connected to a touch electrode for contact with user's hand at an outer perimeter of the handle, and the other pole connected to the electrically conductive shaft by way of a connecting metal part, so as to give a predetermined electric potential to the brush head. This connecting metal part is formed as a contact spring having its one end to slide on the shaft for an electrical connection.

However, the connecting metal part is designed to have a contact portion at its one end for sliding on the shaft, causing unevenness in the electric current flowing within the user's oral cavity by a variance in the electric resistance of the connecting portion between the shaft and the connecting metal part in response to bending of the shaft by user's force toward his/her teeth and deflection of the shaft due to vibration of the shaft during user's tooth brushing.

DISCLOSURE OF THE INVENTION

In view of the above problem, the present invention has been accomplished to provide an electric-electronic toothbrush, which is designed to keep a stable electrical connection between an internal electric source and an electrically conductive shaft driven to vibrate along and/or about its axis, so as to assure a constant supply of an electric current to a user's oral cavity.

The electric-electronic toothbrush in the present invention includes a handle 10 carrying the shaft 30, an actuator 20 which is disposed within the handle and configured to vibrate the shaft along and/or about its axis, a brush head 60 connected to the shaft. The handle 10 is provided on its outer peripheral surface with a touch electrode 14 for contact with a user's hand. The brush head 60 is equipped with a brush electrode 64. The handle 10 is provided with the electric source 12 configured to generate a potential difference between the touch electrode 14 and the brush head 64, so as to flow the electric current into the user's oral cavity through his/her body for removal of tooth plaque. The shaft 30 is electrically conductive, and is coupled by way of an extendible electrically conductive coupler 50;50A to an electrically conductive member 52;13 which is connected to one of poles of the electric source 12. This configuration enables the electric current to flow from within the electric source 12 through the touch electrode 14, user's body, user's teeth, the brush head, the shaft, the electrically conductive coupler, and the electrically conductive member for the purpose of removing tooth plaque, and thereby achieving the electric toothbrush giving combination effect in the removal of tooth plaque caused by the electric current and in teeth brushing due to the vibration of the brush. This electrically conductive coupler 50;50A is secured at its one end to the shaft 30, and at the other end to the electrically conductive member 52;13 located at a predetermined position within the handle 10, so as to absorb vibration of the shaft 30. This configuration enables the shaft to vibrate without negatively affecting the electrical connection between the electric source and the shaft, stabilizing the electric connection, and thereby maintaining the superior effect in the removal of tooth plaque by a desirable electric current flowing into the user's oral cavity.

This electrically conductive coupler 50 is preferably made of an elastic material, such as a coil spring, for effectively absorbing the vibration of the shaft.

Besides, the electrically conductive coupler is preferably formed as a waterproof seal 50A to be provided between the shaft and the handle accommodating therein the shaft. The shaft is arranged to project out through an opening formed at one end of the handle. This waterproof seal is connected at its one end to the shaft, and at the other end to a periphery of the opening of the handle for sealing the opening water-tight, and is electrically connected to the electrically conductive member extending from the electric source within the handle.

More preferably, the electrically conductive coupler 50 is disposed to have its center coincident with an axis core of the shaft 30. With this arrangement, the shaft is kept vibrating about its axis, i.e., free from being deviated therefrom, leaving no undue force which is transmitted from the electrically conductive coupler to act on the bearing, and thereby enabling to keep the shaft stably vibrating.

The actuator includes an electromagnet disposed within the handle, a permanent magnet provided on the shaft, and is configured to vibrate the shaft along and/or about its axis by an alternating electric voltage applied to the electromagnet.

BEST MODE FOR CARRYING OUT THE INVENTION

Figure 1:
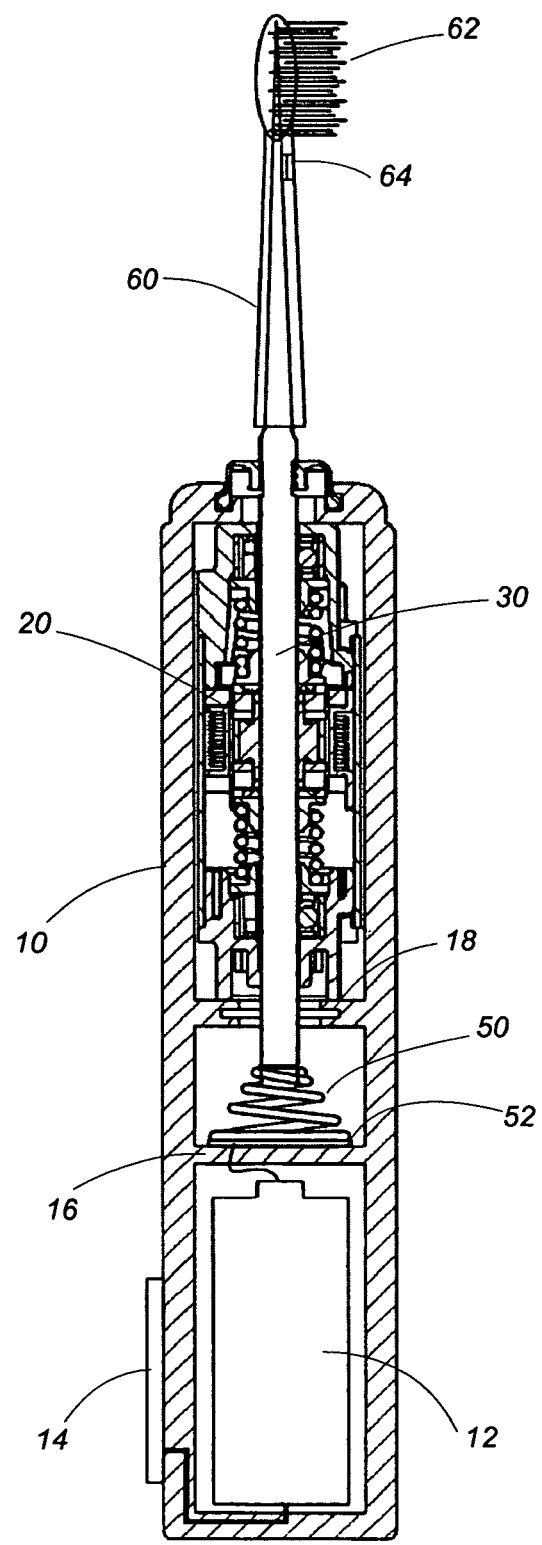
FIG. 1 shows a sectional view of an electric toothbrush in an embodiment of the present invention.

FIG. 1 shows an electric-electronic toothbrush in an embodiment of the present invention. The electric-electronic toothbrush has a cylindrical handle 10 to be grasped by a user's hand, an actuator 20 disposed within the handle 10, a shaft 30 driven to vibrate by the actuator 20, a brush head 60 detachably coupled to the shaft 30. The actuator 20 drives the shaft 30 to vibrate along its axis, so as to vibrate a brush 62 provided at a front end of the brush head 60.

The handle 10 accommodates therein a battery 12 acting as an electric source for driving the actuator 20. The shaft 30 is arranged at its front end to project out through a front end of the handle 10, so as to be coupled to the brush head 60. On a rear end portion of outer peripheral surface of the handle 10 to be in contact with a user's hand, a touch electrode 14 is disposed so as to be connected to a negative pole of the battery 12. The battery 12 is connected at its positive pole to the shaft 30 by way of an electrically conductive coupler 50. The shaft 30 is electrically conductive, and is connected to a conductor (not shown) which extends in its longitudinal direction within the brush head 60. The conductor is formed at its one end as a brush electrode 64, which exposes at a recess formed in the brush head 60 adjacent to the brush 62. With this configuration, an axial portion 64 of the brush head 60 is electrically coupled to the shaft 30 so as to form an electric current path leading to the brush 62. A predetermined electric voltage is applied between the brush electrode 64 and the touch electrode 14 to flow a micro-electric current (e.g., 30 to 50 μA) between user's teeth and the brush head, thereby removing tooth plaque.

Figure 2:
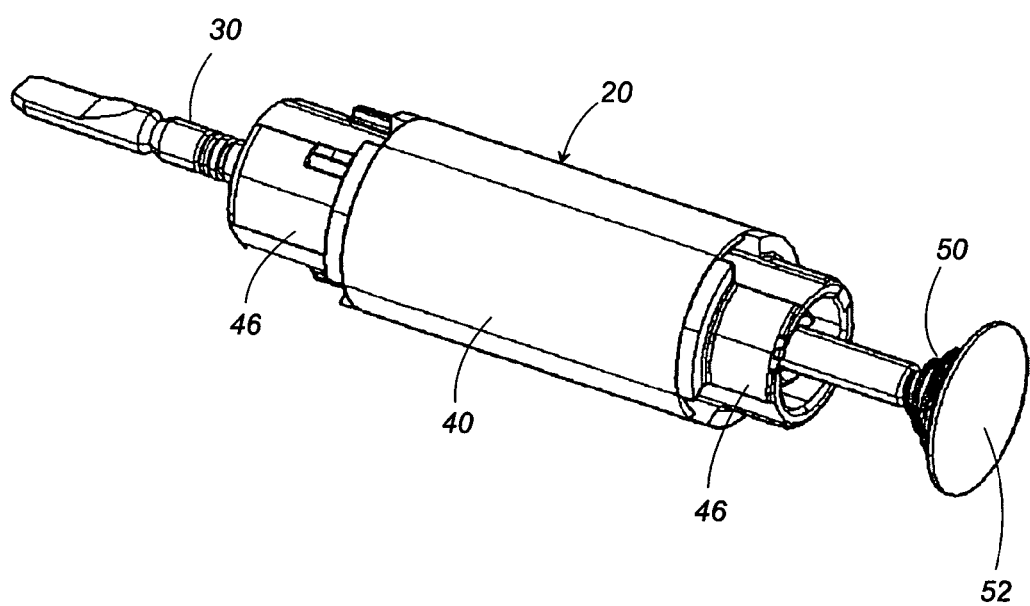
FIG. 2 shows a perspective view of an actuator to be used in the electric toothbrush in the above embodiment of the present invention.
Figure 3:
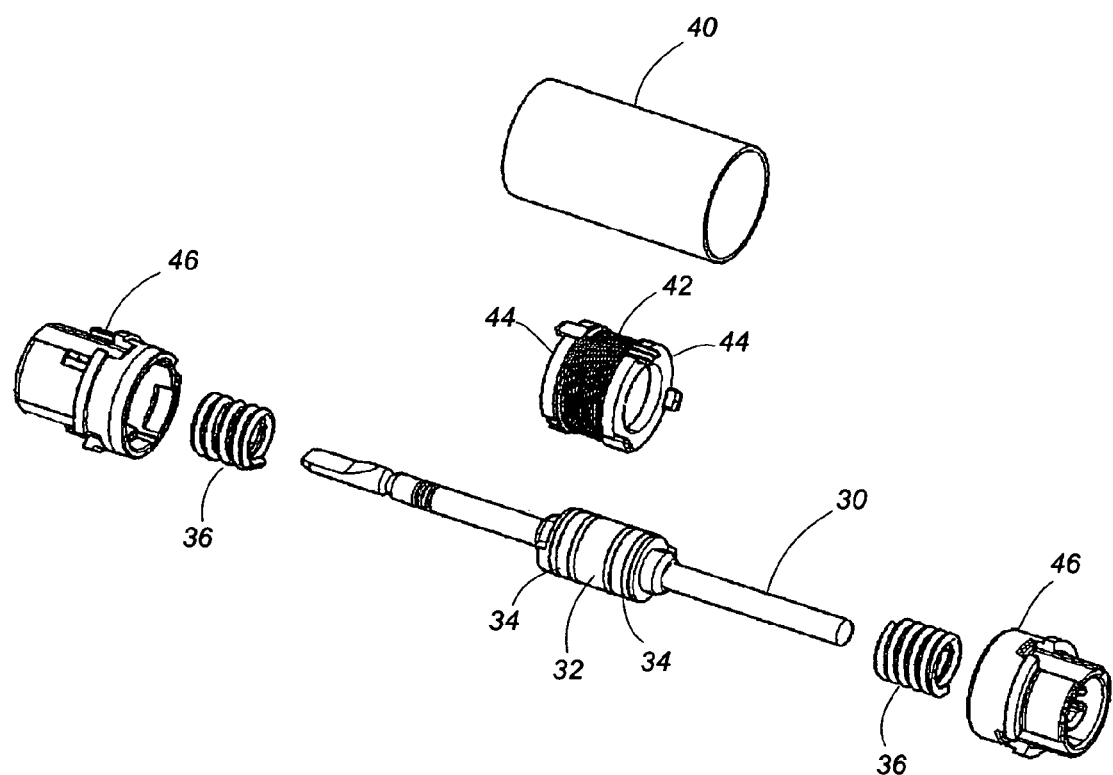
FIG. 3 shows an exploded perspective view of the above actuator in the electric toothbrush in the above embodiment of the present invention.
Figure 4:
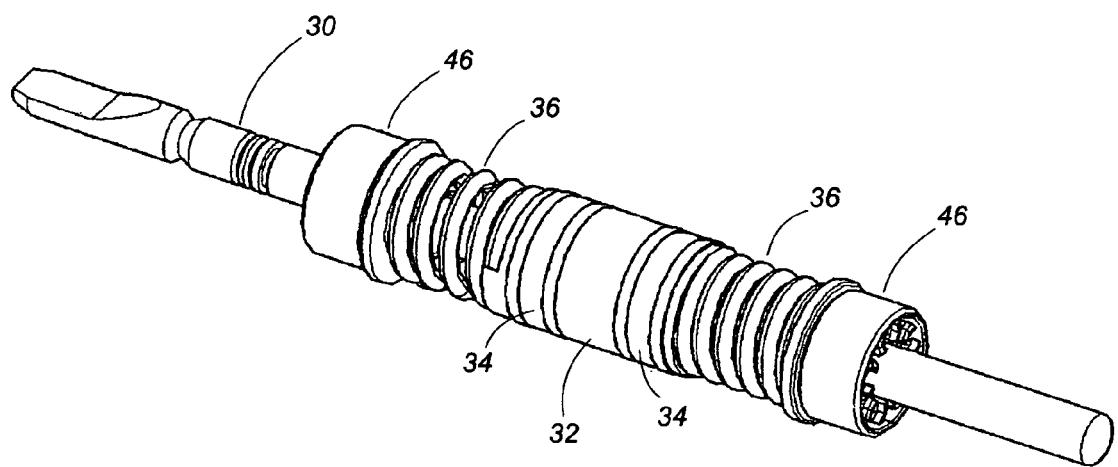
FIG. 4 shows a perspective view of a portion of the above actuator in the electric toothbrush in the above embodiment of the present invention.

As shown in FIGS. 2 to 4, the actuator 20 is equipped with a case 40, which is secured at its both ends with bearings 46 such that the shaft 30 is movably supported to the case 40 along its axis. The shaft 30 is furnished securely at its middle portion with a permanent magnet 32 to be disposed between a pair of yokes 34. Each of coil springs 36 is disposed between the yoke 34 and the bearing 46 so as to form a spring vibration unit of the shaft 30. The case 40 is provided at its middle portion with an electromagnet block for covering therewith the permanent magnet 32 and the yokes 34. The electromagnet block includes a coil 42 and a pair of magnetic pole members 44, so as to vibrate the shaft at a predetermined frequency along its axis due to an interaction between the permanent magnet and a magnetic field generated by an alternating current flowing through the coil. This frequency is set to be a resonance frequency of the electromagnet block. Besides, the alternating current is generated by a control circuit (not shown) triggered by the battery 12 as an electric source.

As shown in FIG. 2, the shaft 30 is connected at its rear end to a disc-shaped electrically conductive member 52 by way of the electrically conductive coupler 50. The electrically conductive member 52 is supported by a separating wall 16 formed within the handle 10, and connected to a positive pole of the battery 12. The electrically conductive coupler 50 is a corn-shaped coil spring, which is connected at its one end to the rear end of the shaft 30 and at the other end to the electrically conductive member 52, so as to absorb the vibration of the shaft 30 along its axis. The shaft 30 is arranged to be rotatable about its axis by the bearings 46, where the rotation about its axis is limited by the coil spring 50. The coil spring 50 has its one end engaged into a groove in the rear end of the shaft 30 so as to be axially and rotatively fixed to the shaft 30. The coil spring may be fixed to the shaft by staking, welding or the like. The shaft 30 is coupled to the positive pole of the battery 12 by way of the elastic and extendible electrically conductive coupler 50 in this embodiment, thereby maintaining the electrical connection between the battery 12 and the shaft 30 for stabilizing the effect in the removal of plaque even when the shaft 30 is tilted by user's teeth brushing. The actuator 20 is assembled together with the shaft 30, the electrically conductive coupler 50, and the electrically conductive member 52 to give a unitary molded structure to be inserted into the handle 10. Herein, the handle 10 is provided therein with a stopper ring 18 through which the shaft 30 is inserted. The stopper ring 18 is designed to limit the rotation of the shaft 30 about its axis.

Figure 5:
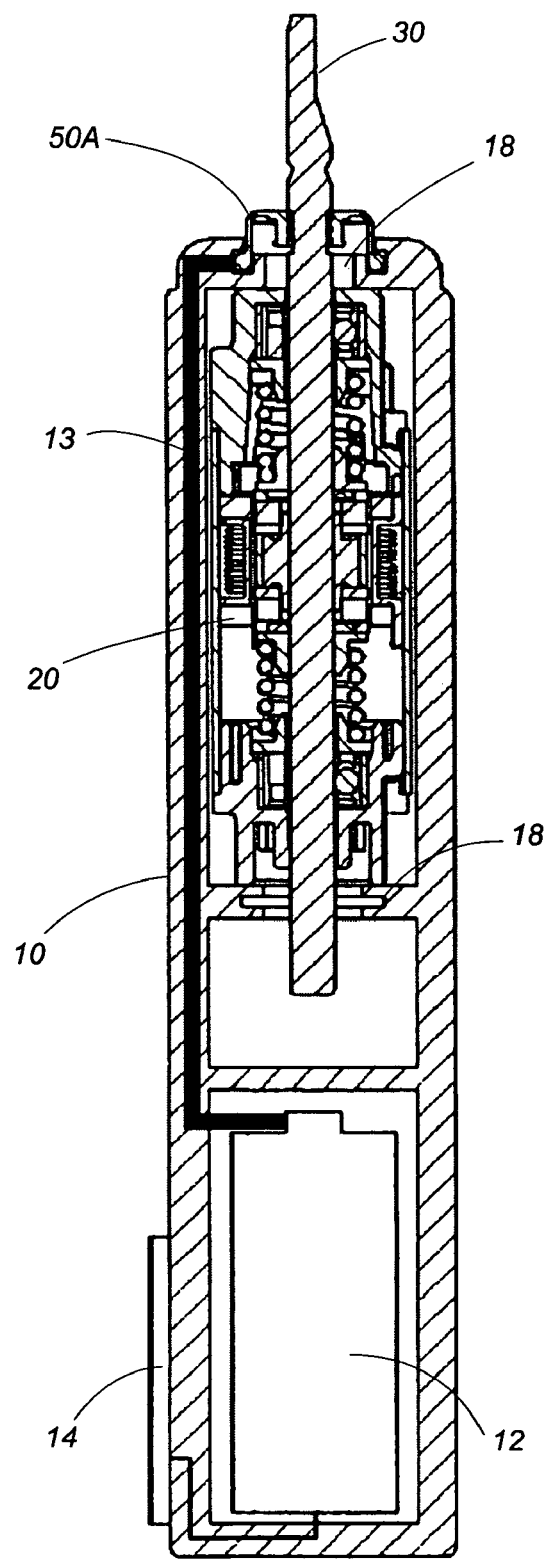
FIG. 5 shows a sectional view of an electric toothbrush in another embodiment of the present invention.

In combination with or instead of making the axial vibration, the actuator 20 may be arranged to vibrate the shaft 30 about its axis. FIG. 5 shows an electric-electronic toothbrush in a second embodiment of the present invention. In this embodiment, a waterproof seal 50A is employed, instead of the coil spring, as the electrically conductive coupler 50. Other components and functions of this embodiment is the same as those of the first embodiment, and thus like parts are designated by like reference numerals and dispensed with duplicate explanations. The waterproof seal 50A is provided to seal watertightly between an opening 18 formed at a front end of the handle 10 and the shaft 30 projecting out through the opening 18. The waterproof seal 50A is formed into a ring-like shape from an elastic and extendible electrically conductive material. The waterproof seal 50A is secured at its inner periphery to the shaft 30, and coupled at its outer periphery to the handle around the opening 18, so as to absorb the vibration along the axis of the shaft 30. The waterproof seal 50A is electrically connected at its outer periphery to a lead wire 13 which is connected to the positive pole of the battery 12, such that the shaft 30 is positively charged to give a positive electrical potential to the brush electrode linked to the shaft 30. In this embodiment, the shaft 30 is designed to vibrate along and about its axis, where the rotation about its axis is limitedly by the stopper ring 18 disposed within the handle 10.

Although the touch electrode 14 is designed to have a negative electrical potential relative to the brush electrode 64 in the above embodiments, the present invention is not limited to the above embodiments. The touch electrode 14 may be arranged to have a positive electrical potential relative to the brush electrode 64.

The invention claimed is:

1. An electric-electronic toothbrush comprising;
    a handle carrying a shaft;
    an actuator being disposed within said handle and configured to vibrate said shaft along and/or about its axis;
    a brush head connected to said shaft;
    a touch electrode disposed on outer peripheral surface of said handle for contact with a user's hand;
    a brush electrode supported to said brush head; and
    an electric source configured to generate a potential difference between said touch electrode and said brush electrode,
    wherein said shaft is electrically conductive, and is coupled by way of an extendible electrically conductive coupler to an electrically conductive member connected to one of poles of said electric source, and
    wherein said electrically conductive coupler is secured at its one end to said shaft, and at the other end to said electrically conductive member located at a predetermined position within said handle.

2. An electric-electronic toothbrush as set forth in claim 1, wherein said electrically conductive coupler is made of an elastic material.

3. An electric-electronic toothbrush as set forth in claim 2, wherein said electrically conductive coupler is a coil spring.

4. An electric-electronic toothbrush as set forth in claim 3, wherein
    said electrically conductive coupler is disposed to have its center coincident with the axis of said shaft.

5. An electric-electronic toothbrush as set forth in claim 1, wherein
    said shaft is arranged to project out through an opening formed at one end of said handle,
    said electrically conductive coupler being a waterproof seal which is coupled at its one end to said shaft and at the other end to a periphery of said opening of said handle for sealing said opening water-tight, and wherein said waterproof seal being electrically connected to said electrically conductive member extending from said electric source within said handle.

6. An electric-electronic toothbrush as set forth in any one of claim 5, wherein
said electrically conductive coupler is disposed to have its center coincident with the axis of said shaft.

7. An electric-electronic toothbrush as set forth in claim 1, wherein
said actuator comprises an electromagnet disposed within said handle and a permanent magnet provided on said shaft, and is configured to vibrate said shaft along its axis in response to an alternating electric voltage applied to said electromagnet.

8. An electric-electronic toothbrush as set forth in claim 1, wherein
said actuator comprises an electromagnet disposed within said handle and a permanent magnet provided on said shaft, and is configured to vibrate said shaft about its axis in response to an alternating electric voltage applied to said electromagnet.

* * * * *